(12) United States Patent
Gong et al.

(10) Patent No.: US 6,652,848 B1
(45) Date of Patent: Nov. 25, 2003

(54) DENDRITIC CELL HYBRIDS

(75) Inventors: Jianlin Gong, Brookline, MA (US); Donald Kufe, Wellesley, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 281 days.

(21) Appl. No.: 09/618,917

(22) Filed: Jul. 18, 2000

Related U.S. Application Data

(63) Continuation of application No. 09/060,603, filed on Apr. 15, 1998, now abandoned.
(60) Provisional application No. 60/043,609, filed on Apr. 15, 1997.

(51) Int. Cl.[7] .......................... A01N 65/00; C12N 5/02; C12N 5/03; C12N 5/04; C12N 5/05; C12N 5/06; C12N 15/02
(52) U.S. Cl. .................. 424/93.1; 435/325; 435/346; 435/347; 435/363; 435/365.1; 435/449
(58) Field of Search ................... 435/449, 346, 435/347, 325, 363, 365.1; 424/93.1

(56) References Cited

U.S. PATENT DOCUMENTS

| | | | |
|---|---|---|---|
| 5,348,878 A | 9/1994 | Rock | |
| 5,851,756 A | 12/1998 | Steinman et al. | 435/2 |

FOREIGN PATENT DOCUMENTS

| | | |
|---|---|---|
| WO | WO 93/20185 | 10/1993 |
| WO | WO 94/28113 | 12/1994 |
| WO | WO 95/16775 | 6/1995 |
| WO | WO 96/07733 | 3/1996 |
| WO | WO 96/30030 | 10/1996 |
| WO | 959676 * | 1/1997 |
| WO | WO 98/17300 | 4/1998 |
| WO | WO 00/57705 | 10/2000 |

OTHER PUBLICATIONS

Cao et al. (1999). *Immunology 97:* 616–625.
Freeman et al. (1993). *Science 262:* 909–911.
Freudenthal and Steinman (1990). *Proc. Natl. Acad. Sci. USA 87:* 7698–7702.
Gong et al. (1998). *Proc. Natl. Acad. Sci. USA 95:* 6279–6283.
Gong et al. (2000). *Proc. Natl. Acad. Sci. USA 97:* 2715–2718.
Gong et al. (2000). *J. Immunol. 165:* 1705–1711.
Inaba et al. (1992). *J. Exp. Med. 176:* 1693–1702.
Kawashima et al. (1998). *Int. J. Cancer 78:* 518–524.
Nabavi et al. (1992). *Nature 360:* 266–268.
Romani et al. (1989). *J. Inv. Derm. 93:* 600–609.
Rosenberg et al. (1998). *Nature Medicine 4:* 321–327.
Sallusto and Lanzavecchia (1994). *J. Exp. Med. 179:* 1109–1118.
Schuler and Steinman (1985). *J. Exp. Med. 161:* 526–546.
Steinman et al. (1979). *J. Exp. Med. 149:* 1–16.
Tsai et al. (1997). *J. Immunol. 158:* 1796–1802.
Wang et al. (1998). *J. Immunol. 161:* 5516–5524.
Young et al. (1992). *J. Clin. Invest. 90:* 229–237.
Fahey et al., "Status of immune–based therapies in HIV infection and AIDS," Clin. Exp. Immunol. 88:1–5, 1992.
Delaney et al., "Xenobiotic, chimerism and the induction of tolerance following organ transplantation," Therapeutic Immunology 1:153–164, 1994.
Orscheschek et al., "An immortalized cell line with features of human follicular dendritic cells. Antigen and cytokine expression analysis." European J. of Immunology 24(11):2682–2690, 1994.
Database Medline PMID 9596976, Zhang et al., Zhonghua Yi Xue Zhi 77(1):39–42 (1997).
Celluzzi et al., J. Investigative Dermatology 108(4):564 (Abstract 157) (1997).
Supplementary European Search Report issued Aug. 31, 2001.
Austyn, J.M., "Accessory cells in culture", Antigen–Presenting Cells, IRL Press, New York, pp. 28–45, 1990.
Bakker et al., "Generation of Antimelanoma Cytotoxic T Lymphocytes from Healthy Donors . . . ", Cancer Research 55:5530–5534, 1995.
Banchereau et al., "Dendritic cells and the control of immunity", Nature 392:246–252, 1998.
Bhardwaj et al., "Dendritic Cells are Potent Antigen–presenting Cells for Microbial Superantigens", J. Exp. Med. 175:267–273, 1992.
Grabbe et al., "Tumor Antigen Presentation by Murine Epidermal Cells", Journal of Immunology 146:3656–3661, 1991.
Gong et al., "Induction of antitumor activity by immunization with fusions . . . ", Nature Medicine 3:558–561, 1997.
Guo et al., "Effective Tumor Vaccine Generated by Fusion of Hepatoma Cells with Activated B Cells", Science 263:518–520, 1994.
Hsu et al., "Vaccination of patients with B–cell lymphoma using autologous antigen–pulsed . . . ", Nature Medicine 2:52–58, 1996.
Inaba et al., "Identification of Proliferating Dendritic Cell Precursors in Mouse Blood", J. Exp. Med. 175:1157–1167, 1992.
Knight et al., "Influence of dendritic cells on tumor growth", Proc. Natl. Acad. Sci. USA 82:4495–4497, 1985.
Komatsubara et al., "Immortalization of Murine Leukocytes by Oncogenes II . . . ", Microbiol. Immunol. 32:869–875, 1988.

(List continued on next page.)

Primary Examiner—Anne M. Wehbé
Assistant Examiner—Q. Janice Li
(74) Attorney, Agent, or Firm—Mintz, Levin, Cohn, Ferris, Glovsky and Popeo P.C.; Ivor R. Elrifi; Christina V. Karnakis

(57) ABSTRACT

Immunostimulatory compositions that contain fused cells formed by fusion between dendritic cells and non-dendritic cells, methods of using these compositions, and methods of generating dendritic cell hybrids.

18 Claims, 3 Drawing Sheets

OTHER PUBLICATIONS

Mayordomo et al., "Bone marrow–derived dendritic cells pulsed with synthetic tumour peptides . . . ", Nature Medicine 1:1297–1302, 1995.

Ohnishi et al., "SV40–adenovirus immortalized cell lines derived from mouse lymphoid dendritic . . . ", Immunology and Cell Biology 73:205–211, 1995.

Paglia et al., "Immortalized Dendritic Cell Line Fully Competent in Antigen Presentation Indicates . . . ", J. Exp. Med. 178:1893–1901, 1993.

Romani et al., "Proliferating Dendritic Cell Progenitors in Human Blood", J. Exp. Med. 180:83–93, 1994.

Rosenzwajg et al., "Human Dendritic Cell Differentiation Pathway From CD34+ . . . ", Blood 87:535–544, 1996.

Thomas et al., "Human Peripheral Blood Dendritic Cell Subsets: Isolation and . . . ", Journal of Immunology 4016–4028, 1994.

Zitvogel et al., "Therapy of Murine Tumors with Tumor Peptide–pulsed Dendritic Cells: . . . ", J. Exp. Med. 183:87–97, 1996.

Houghton et al., "Stuck in the MUC on the long and winding road", Nature Medicine 4:270–271, 1998.

Gong et al., "Induction of antitumor activity by immunization with fusions of . . . ", Abstract No. 4137, Proceedings of the American Association for Cancer Research 38:616, 1997.

Ladyman et al., "Production of monoclonal antibodies", Monoclonal Antibodies: Production, engineering and clinical application, eds. Ritter and Ladyman, pp. 9, 15–17.

Chen et al., "Transduction of Human Dendritic Cells With Tumor Associated Antigen Genes For The Generation of Specific Cytotoxic T Lymphocytes," Proceedings of the American Association for Cancer Research, vol. 38, p. 11, Abstract #72 (1997).

Gimmi et al., "Breast Cancer–Associated Antigen, DF3/MUC1, Induces Apoptosis of Activated Human T Cells," Nature Medicine, vol. 2, No. 12, pp. 1367–1370 (1996).

Gong et al., "Reversal of T Cell Tolerance By Immunization With FC/MUC1 Dendritic–Carcinoma Fusions In MUC1 Transgenic Mice," Proceedings of the American Association For Cancer Rsearch, vol. 39, p. 263, Abstract #1797 (1988).

Gong et al., "Induction of Antigen–Specific Antitumor Immunity With Adenovirus Transduced Dendritic Cells," Gene Therapy, vol. 4, No. 10, pp. 1023–1028 (1997).

Gong et al., "Fusion of human Breast Tumor And Dendritic Cells As Novel Antitumor Vaccine," Proceedings of the American Association for Cancer Research, vol. 39, p. 172, Abstract #1777 (1998).

Yeh et al., Expression of B7–1 By Pam 212 Squamous Cell Carcinoma Enhances Tumor Cell Interactions With Dendritic Epidermal T Cells But Does Not Affect In Vivo Tumor Growth, J. Invest. Dermatol., vol. 109, pp. 728–733 (1997).

* cited by examiner

DENDRITIC CELL HYBRIDS

CROSS REFERENCE TO RELATED APPLICATION

This application is a continuation of U.S. Ser. No. 09/060,603, filed Apr. 15, 1998, now abandoned which claims the benefit of U.S. Ser. No. 60/043,609, filed Apr. 15, 1997, both of which are incorporated herein by reference in their entireties.

FIELD OF THE INVENTION

The invention relates to cellular immunology.

BACKGROUND OF THE INVENTION

Dendritic cells ("DC"s) are potent antigen-presenting cells ("APC"s) in the immune system. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called costimulatory signals, is neither antigen-specific nor MHC-restricted, and can lead to a full proliferation response of T cells and induction of T cell effector functions in the presence of the first type of signals.

Costimulatory signals are generated by interaction between receptor-ligand pairs expressed on the surface of APCs and T cells. One exemplary receptor-ligand pair is one of the B7 costimulatory molecules on the surface of DCs and its counter-receptor CD28 or CTLA-4 on T cells (Freeman et al., Science 262: 909–911, 1993; Young et al., J. Clin. Invest. 90: 229, 1992; Nabavi et al., Nature 360: 266, 1992).

DCs are minor constituents of various immune organs such as spleen, thymus, lymph node, epidermis, and peripheral blood. For instance, DCs represent merely about 1% of crude spleen (Steinman et al., J. Exp. Med. 149: 1, 1979) or epidermal cell suspensions (Schuler et al., J. Exp. Med. 161: 526, 1985; and Romani et al., J. Invest. Dermatol. 93: 600, 1989), and 0.1–1% of mononuclear cells in peripheral blood (Freudenthal et al., Proc. Natl. Acad. Sci. USA 87: 7698, 1990). Methods for generating dendritic cells from peripheral blood or bone marrow progenitors have been described (Inaba et al., J. Exp. Med. 175: 1157, 1992; Inaba et al., J. Exp. Med. 176: 1693–1702, 1992; Romani et al., J. Exp. Med. 180: 83–93, 1994; and Sallusto et al., J. Exp. Med. 179: 1109–1118, 1994).

SUMMARY OF THE INVENTION

The invention features compositions for stimulating an immune system. These compositions each contain a plurality of cells at least half of which (e.g., more than 70–80%) are fused cells, each of which fused cells is generated by fusion between at least one mammalian dendritic cell (e.g., a DC derived from a bone marrow culture or a peripheral blood cell culture) and at least one mammalian non-dendritic cell (e.g., a cancer cell or a transfected cell) that expresses a cell-surface antigen (e.g., a cancer antigen). By "cancer antigen" is meant an antigenic molecule that is expressed primarily or entirely by cancer cells, as opposed to normal cells in an individual bearing the cancer. At least half (e.g., at least 70%, and preferably at least 80%) of the fused cells in the compositions express, in an amount effective to stimulate an immune system (e.g., to activate T cells), MHC class II molecules, B7, and the cell-surface antigen. By "B7" is meant any member (e.g., B7-1 or B7-2) of the B7 family of costimulatory molecules.

The parental cells used to generate the fused cells can be obtained from a single individual (e.g., a human, a mouse, or a rat). They can also be obtained from different individuals of the same species (e.g., *homo sapiens*), with matching or non-matching MHC molecules.

Also embraced by the invention are methods of producing fused cells. In these methods, mammalian dendritic cells are fused with mammalian non-dendritic cells expressing a cell-surface antigen in the presence of a fusion agent (e.g., polyethylene glycol or Sendai virus). After culturing the post-fusion cell mixture in a medium (which optionally contains hypoxanthine, aminopterin and thymidine) for a period of time (e.g., 5–12 days), the cultured fused cells are separated from unfused parental non-dendritic cells, based on the different adherence properties of the two cell groups. The unfused parental dendritic cells do not proliferate, and so die off. Even if they remain present in the therapeutic composition, they will not interfere with the effects of the fused cells. The isolated fused cells, which typically express (a) MHC class II protein, (b) B7, and (c) the cell-surface antigen on the non-dendritic parental cells, are useful for stimulating an immune system.

The invention also provides methods of maintaining the DC phenotype of a fused cell by re-fusing it with at least one additional mammalian dendritic cell. The re-fused cells express MHC class II molecules, B7, and the cell-surface antigen of the dendritic parental cells, and are useful for stimulating an immune system.

The compositions of the invention can be administered to an individual (e.g., a human) to stimulate the individual's immune system. This individual may need an immune stimulation due to infection, or susceptibility to infection, with an intracellular pathogen; cancer; or predisposition to develop cancer. The DCs used to generate fused cells can be obtained from this individual. If this individual has cancer, the individual's own cancer cells can be used for fusion with his or her own DCs to generate fused cells, which are then administered to the individual.

Stimulation of the immune system with DC fusion cells results in enhancement of the individual's immunity against a disease condition characterized by abnormal expression of a cell surface antigen that is also present on the parental non-dendritic partners of the fusion cells. Abnormal expression means that the cell surface antigen (i) is not expressed in normal tissue, (ii) is expressed at a much higher level in diseased cells of a given tissue type than in normal tissue of the same type, or (iii) is modified (e.g., phosphorylated) differently in diseased cells of a given tissue type than in normal cells of the same type. Enhancement of immunity entails enhancement of the immune system's cell-mediated or humoral functions, or both.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and other references mentioned herein are incorporated by reference in their entirety. In case of conflict, the present specification, including definitions, will control. The materials, methods, and examples are illustrative only and not intended to be limiting.

Other features and advantages of the invention will be apparent from the following drawings, detailed description, and from the claims.

DETAILED DESCRIPTION OF THE INVENTION

Figure 1A:
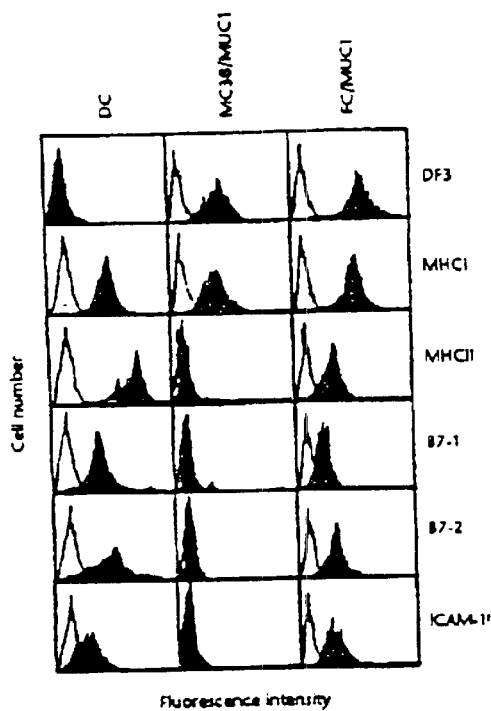
FIG. 1A is a graph showing the results of flow cytometric analysis of the indicated antigens on the surface of DCs (DC), MC38 cells (MC38/MCU1) and fused cells generated by fusion between DCs and MC38/MUC1 cells (FC/MCU1).

The invention features (1) immune system-stimulating compositions that contain fused cells formed by fusion between DCs and non-dendritic cells; (2) methods of stimulating an immune system with the compositions; and (3) methods of generating the fused cells.

DCs can be obtained from bone marrow cultures, peripheral blood, spleen, or other appropriate tissue of a mammal using protocols known in the art. Bone marrow contains DC progenitors, which, upon treatment with cytokines such as granulocyte-macrophage colony-stimulating factor ("GM-CSF") and interleukin 4 ("IL-4"), proliferate and differentiate into DCs. DCs so obtained are relatively immature (as compared to, for instance, spleen DCs). As discovered by Applicants, these immature DCs are more amenable to fusion than the more mature DCs found in spleen. Peripheral blood also contains relatively immature DCs or DC progenitors, which can propagate and differentiate in the presence of appropriate cytokines such as GM-CSF and which can also be used in fusion.

The non-dendritic cells used in the invention can be derived from any tissue or cancer by well known methods and can be immortalized. Non-dendritic cells expressing a cell-surface antigen of interest can be generated by transfecting the non-dendritic cells of a desired type with a nucleic acid molecule that encodes a polypeptide comprising the antigen. Exemplary cell-surface antigens are MUC1, α-fetoprotein, γ-fetoprotein, carcinoembryonic antigen, fetal sulfoglycoprotein antigen, $α_2$H-ferroprotein, placental alkaline phosphatase, and leukemia-associated membrane antigen. Methods for transfection and identifying antigens are well known in the art.

Fusion between the DCs and the non-dendritic cells can be carried out with well-known methods such as those using polyethylene glycol ("PEG") or Sendai virus. The ratio of DCs to non-dendritic cells in fusion can vary from 1:100 to 1000:1, with a ratio higher than 1:1 being preferred where the non-dendritic cells proliferate heavily in culture. After fusion, unfused DCs usually die off in a few days in culture, and the fused cells can be separated from the unfused parental non-dendritic cells by the following two methods, both of which yield fused cells of approximately 50% or higher purity, i.e., the fused cell preparations contain less than 50%, and often less than 30%, unfused cells.

If the non-dendritic cells die or at least fail to proliferate in the presence of a given reagent and this sensitivity can be overcome by the fusion with DCs, the post-fusion cell mixtures containing the fused as well as the parental cells may be incubated in a medium containing this reagent for a period of time sufficient to eliminate most of the unfused cells. For instance, a number of tumor cell lines are sensitive to HAT due to lack of functional hypoxanthine-guanine phosphoribosyl transferase ("HGPRT") Fused cells formed by DCs and these tumor cell lines become resistant to HAT, as the DCs contribute functional HGPRT. Thus, a HAT selection can be performed after fusion to eliminate unfused parental cells. Contrary to standard HAT selection techniques, the HAT selection generally should not last for more than 12 days, since Applicants find that lengthy culturing leads to loss of MHC class II protein and/or B7 costimulatory molecules on the fused cells.

The second method of separating unfused cells from fused cells is based on the different adherence properties between the fused cells and the non-dendritic parental cells. It has been found that the fused cells are generally lightly adherent to tissue culture containers. Thus, if the non-dendritic parental cells are much more adherent, e.g., in the case of carcinoma cells, the post-fusion cell mixtures can be cultured in an appropriate medium (HAT is not needed but may be added if it slows the growth of unfused cells) for a short period of time (e.g., 5–10 days). Subsequently, the fused cells can be gently dislodged and aspirated off, while the unfused cells grow firmly attached to the tissue culture containers. Conversely, if the non-dendritic parental cells grow in suspension, after the culture period, they can be gently aspirated off while leaving the fused cells loosely attached to the containers.

Fused cells obtained by the above-described methods typically retain the phenotypic characteristics of DCs. For instance, these fused cells express T-cell stimulating molecules such as MHC class II protein, B7-1, B7-2, and adhesion molecules characteristic of APCs such as ICAM-1. The fused cells also continue to express cell-surface antigens of the parental non-dendritic cells, and are therefore useful for inducing immunity against the cell-surface antigens. Notably, when the non-dendritic fusion partner is a tumor cell, the tumorigenicity of the fused cell is often found to be attenuated in comparison to the parental tumor cell.

In the event that the fused cells lose certain DC characteristics such as expression of the APC-specific T-cell stimulating molecules, they (i.e., primary fused cells) can be refused with dendritic cells to restore the DC phenotype. The refused cells (i.e., secondary fused cells) are found to be highly potent APCs, and in some cases, have even less tumorigenicity than primary fused cells. The fused cells can be refused with the dendritic or non-dendritic parental cells as many times as desired.

Fused cells that express MHC class II molecules, B7, or other desired T-cell stimulating molecules can also be selected by panning or fluorescence-activated cell sorting with antibodies against these molecules.

The fused cells of the invention can be used to stimulate the immune system of a mammal for treatment or prophylaxis of a disease. For instance, to treat a tumor (primary or metastatic) in a human, a composition containing fused cells formed by his own DCs and tumor cells can be administered to him, e.g., at a site near the lymphoid tissue. The composition may be given multiple times (e.g., three to five times) at an appropriate interval (e.g., every two to three weeks) and dosage (e.g., approximately $10^5$–$10^8$, e.g., about 0.5× $10^6$ to 1×$10^6$, fused cells per administration). For prophylaxis (i.e., vaccination) against cancer, non-syngeneic fused cells such as those formed by syngeneic DCs and allogeneic or xenogeneic cancer cells, or by allogeneic DCs and cancer cells, can be administered. To monitor the effect of vaccination, cytotoxic T lymphocytes obtained from the treated individual can be tested for their potency against cancer cells in cytotoxic assays. Multiple boosts may be needed to enhance the potency of the cytotoxic T lymphocytes. Example I below demonstrates that fusion cells formed by tumor cells and syngeneic DCs can prevent and treat tumors in animal models. Example III further demonstrates that such fusion cells may even activate anergized T cells that are specific for tumor antigens.

Cells infected with an intracellular pathogen can also be used as the non-dendritic partner of the fusion for treatment of the disease caused by that pathogen. Examples of pathogens include, but are not limited to, viruses (e.g., human immunodeficiency virus, hepatitis A, B, or C virus, papilloma virus, herpes virus, or measles virus), bacteria (e.g., *Corynebacterium diphtheria, Bordetella pertussis*), and intracellular eukaryotic parasites (e.g., Plasmodium spp., Schistosoma spp., Leishmania spp., Trypanosoma spp., or *Mycobacterium lepre*). Compositions containing the appropriate fused cells are administered to an individual (e.g., a human) in a regimen determined as appropriate by a person skilled in the art. For example, the composition may be given multiple times (e.g., three to five times) at an appropriate interval (e.g., every two to three weeks) and dosage (e.g., approximately $10^5$–$10^8$, and preferably about $10^7$ fused cells per administration).

Alternatively, non-dendritic cells transfected with one or more nucleic acid constructs each of which encodes one or more identified cancer antigens or antigens from a pathogen can be used as the non-dendritic partner in fusion. These antigens need not be expressed on the surface of the cancer cells or pathogens, so long as the antigens can be presented by a MHC class I or II molecule on the fused cells. Fused cells generated by DCs and these transfected cells can be used for both treatment and prophylaxis of cancer or a disease caused by that pathogen. By way of example, fusion cells expressing MUC1 can be used to treat or prevent breast cancer, ovarian cancer, pancreatic cancer, prostate gland cancer, lung cancer, and myeloma; fusion cells expressing α-fetoprotein can be used to treat or prevent hepatoma or chronic hepatitis, where α-fetoprotein is often expressed at elevated levels; and fusion cells expressing prostate-specific antigen can be used to treat prostate cancer. Methods of transfection and identifying antigens are well known in the art. Administration of compositions containing the fused cells so produced is as described above.

The following examples are meant to illustrate, but not limit, the compositions and methods of the invention.

EXAMPLE I

Fusion of Mouse

Dendritic Cells and Non-Dendritic Cells

Materials and Methods

Cell Culture and Fusion

Murine (C57BL/6) MC38 adenocarcinoma cells were stably transfected with the DF3/MUC1 cDNA to generate the MC38/MUC1 cell line (Siddiqui et al., Proc. Natl. Acad. Sci. USA 85:2320–2323, 1988; Akagi et al., J. Immunother. 20:38–47, 1997). MC38, MC38/MUC1 and the syngeneic MB49 bladder cancer cells were maintained in DMEM supplemented with 10% heat-inactivated fetal calf serum ("FCS"), 2 mM glutamine, 100 U/ml penicillin and 100 μg/ml streptomycin.

DCs were obtained from bone marrow culture using a method described by Inaba et al. (J. Exp. Med. 176:

1693–1702, 1992) with modifications. In brief, bone marrow was flushed from long bones, and red cells were lysed with ammonium chloride. Lymphocytes, granulocytes, and $Ia^{30}$ cells were depleted from the bone marrow cells by incubation with the following monoclonal antibodies ("mAb"s):

(1) 2.43, anti-CD8 [TIB 210; American Type Culture Collection (ATCC), Rockville, Md.];
(2) GK1.5, anti-CD4 (TIB 207, ATCC);
(3) RA3-3A1/6.1, anti B220/CD45R (TIB 146, ATCC);
(4) B21-2, anti-Ia (TIB 229, ATCC); and
(5) RB6-8C5, anti-Gr-1 (Pharmingen, San Diego, Calif.);

and then complement. The unlysed cells were plated in six-well culture plates in RPMI 1640 medium supplemented with 5% heat-inactivated FCS, 50 $\mu$M 2-mercaptoethanol, 1 mM HEPES (pH 7.4), 2 mM glutamine, 10 U/ml penicillin, 10 $\mu$g/ml streptomycin and 500 U/ml recombinant murine GM-CSF (Boehringer Mannheim, Ind.). At day 7 of culture, nonadherent and loosely adherent cells were collected and replated in 100-mm petri dishes ($10^6$ cells/ml; 8 ml/dish) The nonadherent cells were washed away after 30 min of incubation and RPMI medium containing GM-CSF was added to the adherent cells. After 18 hours in culture, the nonadherent cell population was removed for fusion with MC38/MUC1 cells or MC38.

Fusion was carried out by incubating cells with 50% PEG in Dulbecco's phosphate buffered saline ("PBS") without $Ca^{2+}$ or $Mg^{2+}$ at pH 7.4. The ratio of DCs to tumor cells in the fusion was from 15:1 to 20:1. After fusion, the cells were plated in 24-well culture plates in a medium containing HAT (Sigma) for 10–14 days. Because MC38 cells are not very sensitive to HAT, HAT was used to slow the proliferation of, rather than kill, MC38/MUC1 and MC38 cells. MC38/MUC1 and MC38 cells grow firmly attached to the tissue culture flask, while the fused cells were dislodged by gentle pipetting.

Flow Cytometry

Cells were washed with PBS and incubated with mAb DF3 (anti-MCU1), mAb M1/42/3.9.8 (anti-MHC class I), mAb M5/114 (anti-MHC class II), mAb 16-10A1 (anti-B7-1), mAb GL1 (anti-B7-2) and MAb $3E^2$ (anti-ICAM-1) for 30 min on ice. After washing with PBS, fluorescein isothiocyanate ("FITC")-conjugated anti-hamster, -rat and -mouse IgG was added for another 30 min on ice. Samples were then washed, fixed and analyzed by FACSCAN (Becton Dickinson, Mount View, Calif.).

Cytotoxic T Cell Activity

Cytotoxic T cell ("CTL") activity was determined by the release of lactate dehydrogenase ("LDH") (CytoTox, Promega, Madison, Wis.).

Mixed Leukocyte Reactions

The DCs, MC38/MCU1 and FC/MUC1 cells were exposed to ionizing radiation (30 Gy) and added to $1 \times 10^5$ syngeneic or allogeneic T cells in 96-well flat-bottomed cultured plates for 5 days. The T cells were prepared by passing spleen suspensions through nylon wool to deplete residual APCs and plated to 90 min in 100 mm tissue culture dishes. $^3$[H]-thymidine uptake in nonadherent cells was measured at 6 h after a pulse of 1 $\mu$Ci/well (GBq/mmol; Du Pont-New England Nuclear, Wilmington, Del.). Each reaction was performed in triplicate.

In Vivo Depletion of Immune Cell Subsets

Mice were injected both intravenously and intraperitoneally every other day with mAb GK1.5 (anti-CD4), mAb 2.43 (anti-CD8) or rat IgG 4 days before the first of two immunizations with FC/MUC1 through 4 days before challenge with MC38/MUC1 cells. The splenocytes were harvested for flow cytometry and analysis of CTL activity.

Results

Murine MC38 adenocarcinoma cells were fused to bone marrow-derived DCs. To demonstrate successful fusions, MC38 cells that stably express the DF3/MUC1 tumor-associated antigen were first used (Siddiqui et al., Proc. Natl. Acad. Sci. USA 75: 5132–5136, 1978). The fusion cells (FC/MUC1) expressed DF3/MUC1, as well as MHC class I and II, B7-1, B7-2 and ICAM-1 (FIG. 1A).

Figure 1B:
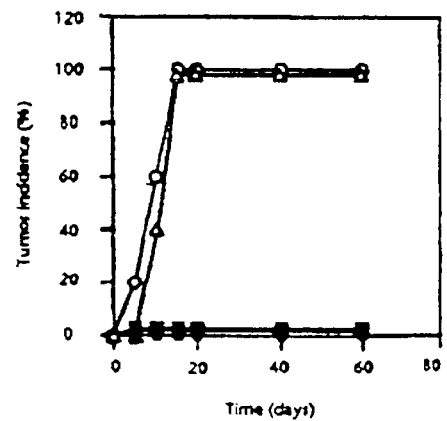
FIG. 1B is a graph showing tumor incidence in female C57BL/6 mice (10 per group) injected subcutaneously with $2\times10^5$ MC38/MUC1 cells (○), $2\times10^6$ DCs mixed with $2\times10^5$ MC38/MUC1 cells (Δ), $2\times10^5$ FC/MUC1 cells (●), or $5\times10^5$ FC/MUC1 cells (■). Tumor incidence (>3 mm in diameter) was monitored at the indicated days after injection. Similar results were obtained in three separate experiments.

Moreover, most of the fusion cells exhibited a DC morphology with veiled processes and dendrites. Fusions of MC38 cells with DCs (FC/MC38) resulted in similar patterns of cell-surface antigen expression with the exception of no detectable DF3/MUC1 antigen. Injection of MC38/MUC1 cells in mice resulted in the formation of subcutaneous tumors (FIG. 1B). Similar findings were obtained with MC38/MUC1 cells mixed with DCs (FIG. 1B) or after mixing MC38 cells with DCs. However, the finding that no tumors formed in mice injected with FC/MUC1 indicated that the fusion cells are not tumorigenic (FIG. 1B).

Figure 1C:
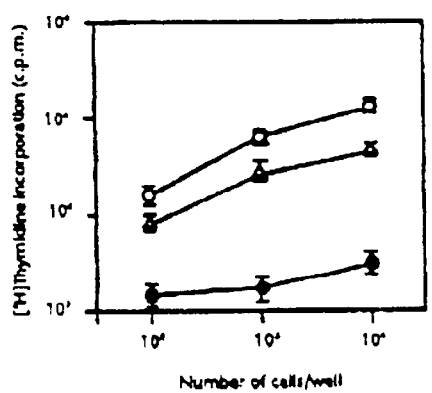
FIG. 1C is a graph showing [$^3$H]-thymidine incorporation in mixed leukocyte reactions. DCs (○), MC38/MUC1 cells (●), and FC/MUC1 cells (Δ) were irradiated (30 Gy) and added at the indicated ratios to $1\times10^5$ allogeneic Balb/c T cells. [$^3$H]-Thymidine uptake at 6 h of incubation is expressed as the mean±s.e.m. of three determinations. Similar results were obtained in three separate experiments.

Dendritic cells are potent stimulators of primary MLRs; Steinman et al., Proc. Natl. Acad. Sci. U.S.A. 75: 5132–5136, 1978; van Voorhis et al., J. Exp. Med. 158: 174–191, 1983) and induce the proliferation of allogeneic $CD8^+$ T cells in vitro (Inaba et al., J. Exp. Med. 166: 182–194, 1987; Young et al., J. Exp. Med. 171: 1315–1332, 1990). To characterize in part the function of FC/MUC1 cells, their effect in primary allogeneic MLRs was compared with the effect of DC and MC38/MUC1 cells. The results demonstrate that, like DCs, FC/MUC1 cells exhibit a stimulatory function in allogeneic MLR (FIG. 1C). By contrast, MC38/MUC1 cells had little effect on T cell proliferation (FIG. 1C).

Figure 2A:
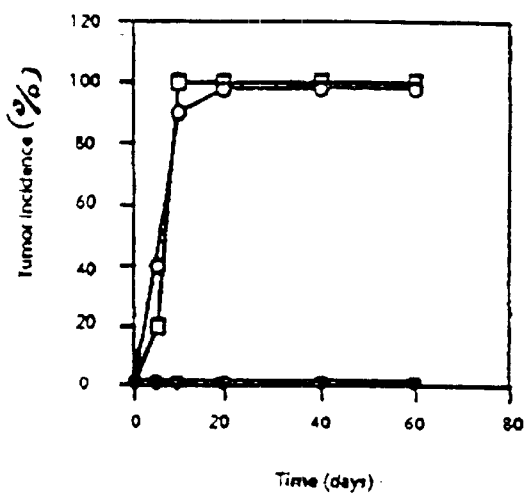
FIG. 2A is a graph showing induction of anti-tumor activity by FC/MUC1 in the form of percent tumor incidence. Groups of 10 mice were injected subcutaneously twice at 14-day intervals $3\times10^5$ DC (○), $3\times10^5$ FC/MUC1 (●), or PBS (□). After 14 days, the mice were challenged subcutaneously with $2.5\times10^5$ MC38/MUC1 cells. Tumors >3 mm in diameter were scored as positive. Similar results were obtained in three separate experiments.

Mice were immunized twice with FC/MUC1 cells to assess in vivo function. Tumors developed in mice that had been immunized twice with $10^6$ irradiated MC38/MUC1 cells and subsequently challenged with MC38/MUC1 cells (Table 1). In contrast, after immunization with $2.5 \times 10^5$ FC/MUC1 cells, all animals remained tumor-free after challenge with MC38/MUC1 cells (FIG. 2A and Table 1). Control animals immunized with DCs alone or PBS and then challenged subcutaneously with $2.5 \times 10^5$ MC38 or MC38/MUC1 cells, however, exhibited tumor growth within 10–20 days (FIG. 2A).

Figure 2B:
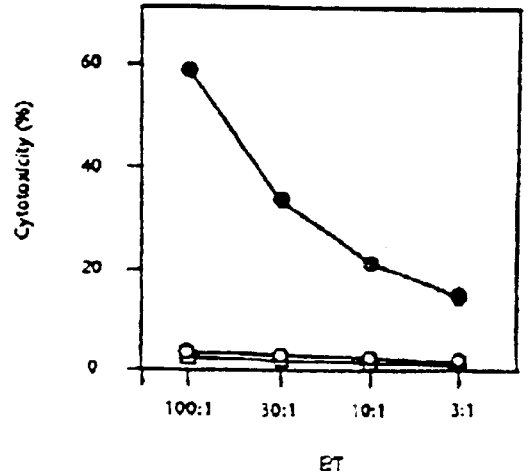
FIG. 2B is a graph showing induction of anti-tumor activity by FC/MUC1 in the form of cytotoxicity. Mice injected twice with DC (○), FC/MUC1 (●) or PBS (□) were challenged with $2.5\times10^5$ MC38/MUC1 tumor cells. Splenocytes were isolated at 20 days after challenge and incubated at the indicated effector:target ratios with MC38/MUC1 target cells. Cytotoxic T lymphocyte ("CTL") activity (mean±s.e.m.) was determined by the 4-h LDH release assay. Similar results were obtained in three separate experiments.

Moreover, immunization with FC/MUC1 or FC/MC38 had no detectable effect on growth of unrelated syngeneic MB49 bladder carcinoma (Table 1). CTLs from mice immunized with FC/MUC1 cells induced lysis of MC38/MUC1, but not MB49 cells (FIG. 2B). By contrast, CTLs from mice immunized with DCs or PBS exhibited no detectable lysis of the MC38/MUC1 targets (FIG. 2B).

Figure 2C:
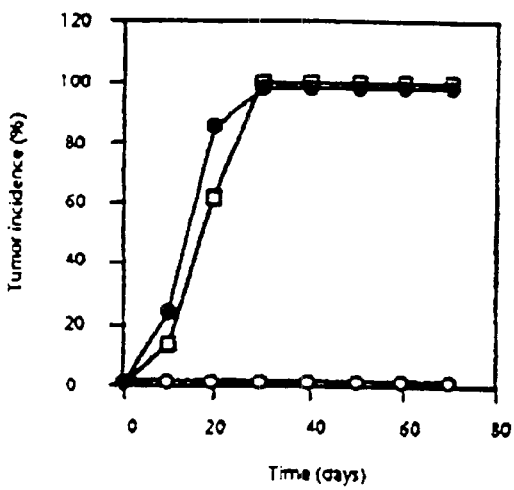
FIG. 2C is a graph showing induction of anti-tumor activity by FC/MUC1 in the form of percent tumor incidence. Mice (8 per group) were injected intravenously and intraperitoneally every other day with mAbs against $CD4^+$ (□) and $CD8^+$ (●) cells beginning 4 days before the first of two immunizations with FC/MUC1 and continuing until 4 days before challenge with $5\times10^5$ MC38/MUC1 cells. Rat IgG (○) was injected as a control. Tumors of >3 mm were scored as positive. Similar results were obtained in two separate experiments.
Figure 2D:
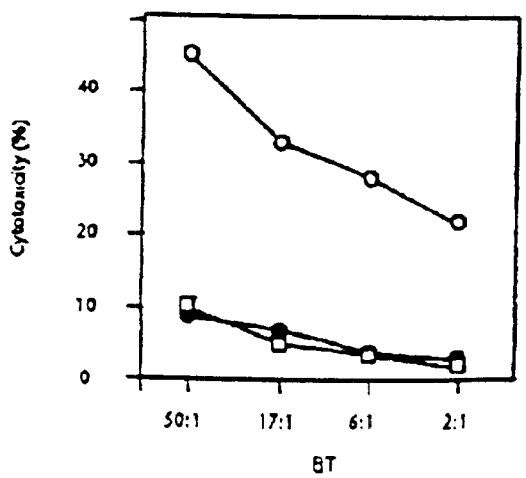
FIG. 2D is a line graph showing induction of anti-tumor activity by FC/MUC1 in the form of cytotoxicity. Mice were treated as above with mAbs against $CD4^+$ (□) and $CD8^+$ (●), rat IG (○), immunized with FC/MUC1 and then challenged with MC38/MUC1 cells. Splenocytes were harvested at 20 days after tumor challenge and incubated with MC38/MUC1 cells. CTL activity (mean±s.e.m.) was determined by the 4-h LDH release assay. Similar results were obtained in three separate experiments.

To further define the effector cells responsible for antitumor activity, mice were injected intraperitoneally with antibodies against $CD4^+$ or $CD8^+$ cells before and after immunization with FC/MUC1. Depletion of the respective population by 80–90% was confirmed by flow cytometric analysis of splenocytes. The finding that injection of anti-CD4 and anti-CD8 antibodies increases tumor incidence indicated that both $CD4^+$ and $CD8^+$ T cells contributed to antitumor activity (FIG. 2C). Moreover, depletion of $CD4^+$ and $CD8^+$ T cells was associated with reduced lysis of MC38/MUC1 cells in vitro (FIG. 2D).

TABLE 1

Potency and specificity of antitumor immunity induced with fusion cells

| Immunogen | Tumor Challenge | Animals with tumor |
|---|---|---|
| a, Irradiated MC38/MUC1 ($1 \times 10^6$) | MC38/MUC1 ($1 \times 10^6$) | 2/3 |
| | M C38/MUC1 ($2 \times 10^6$) | 3/3 |
| b, FC/MUC1 ($2.5 \times 10^5$) | MC38/MUC1 ($1 \times 10^6$) | 0/10 |
| | MC38/MUC1 ($2 \times 10^6$) | 0/10 |
| | MB49 ($5 \times 10^6$) | 6/6 |
| c, FC/MC38 ($2.5 \times 10^5$) | MC38 ($1 \times 10^6$) | 0/6 |
| | MB49 ($5 \times 10^5$) | 6/6 |

Figure 3B:
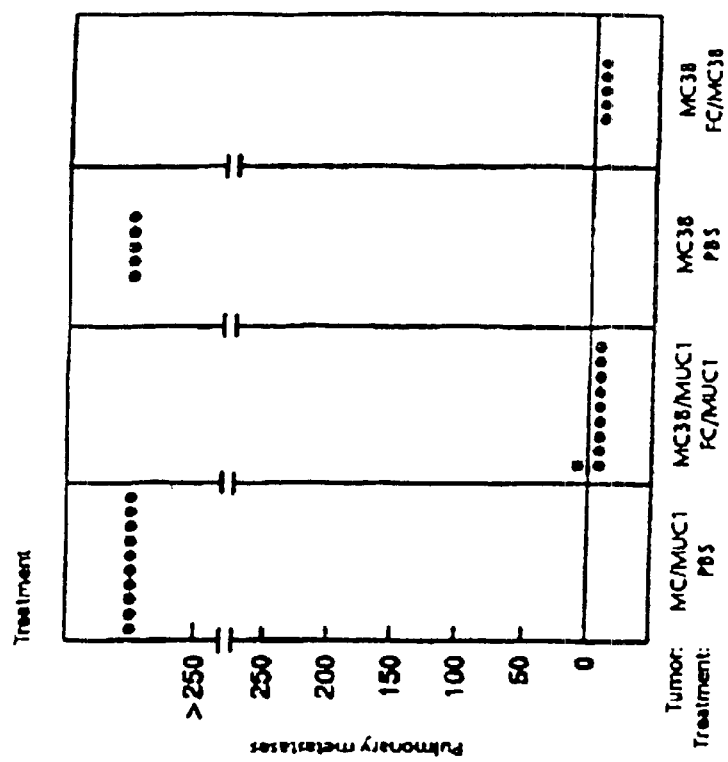
FIG. 3B is a graph showing treatment of MC38/MUC1 pulmonary metastases after immunization with FC/MUC1. Groups of 10 mice were injected intravenously with $1\times10^6$ MC38/MUC1 cells or MC38 cells. The mice were immunized with $1\times10^6$ FC/MUC1 or FC/MC38 at 4 and 18 days after tumor challenge and then sacrificed after an additional 10 days. Pulmonary metastases were enumerated for each mouse. Similar results were obtained in two separate experiments (10/10 mice treated with FC/MUC1 had no pulmonary metastases in the second experiment).
Figure 3A:
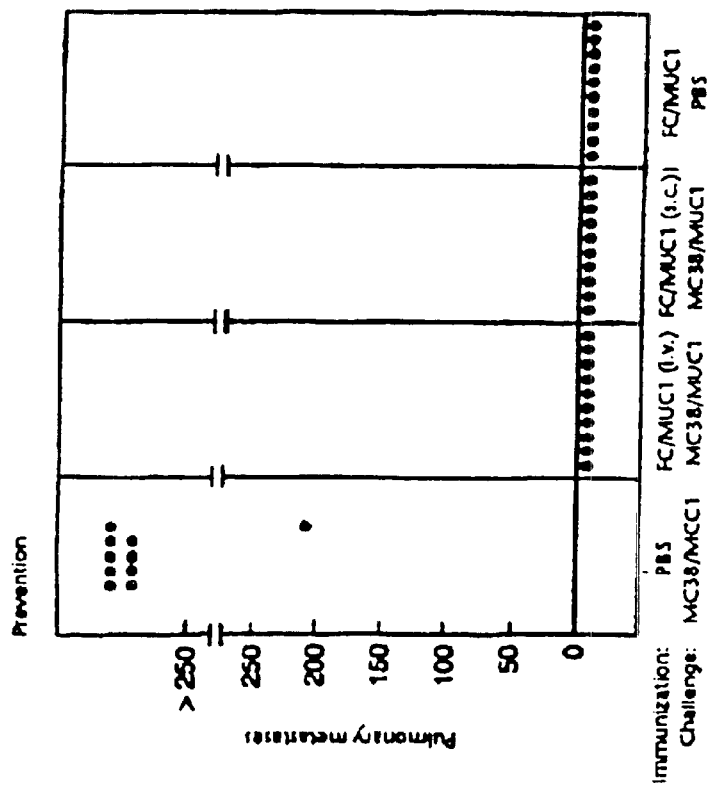
FIG. 3A is a graph showing prevention of MC38/MUC1 pulmonary metastases after immunization with FC/MUC1. Groups of 10 mice were injected twice with FC/MUC1 cells or PBS and then challenged after 14 days with intravenous administration of $1\times10^6$ MC38/MUC1 cells. The mice were sacrificed 28 days after challenge. Pulmonary metastases were enumerated after staining the lungs with India ink (Wexler, J. Natl. Cancer Inst. 36: 641–643, 1966).

The numbers in parentheses represent cells used for immunization or tumor challenge To determine whether immunization with FC/MUC1 cells is effective for the prevention of disseminated disease, a model of MC38/MUC1 pulmonary metastases was used. Immunization with FC/MUC1 intravenously or subcutaneously completely protected against intravenous challenge with MC38/MUC1 cells (FIG. 3A). By contrast, all unimmunized mice similarly challenged with MC38/MUC1 cells developed over 250 pulmonary metastases (FIG. 3A).

In a treatment model, MC38/MUC1 pulmonary metastases were established 4 days before immunization with FC/MUC1. While control mice treated with vehicle developed over 250 metastases, nine out of ten mice treated with FC/MUC1 cells had no detectable metastases and one mouse had fewer than 10 nodules (FIG. 3B). Mice treated with FC/MC38 cells similarly had no detectable MC38 pulmonary metastases (FIG. 3B). These findings indicated that FC/MUC1 immunization can be used for both the prevention and treatment of metastatic disease.

EXAMPLE II

Fusion of Human DCs and Myeloma Cells

Materials and Methods

Leukocytes in buffy coats (or leukopacks) obtained by leukophoresis were fractionated by centrifugation in Ficoll. The fraction containing (peripheral blood) mononuclear cells was incubated in a flask containing RPMI 1640 supplemented with 10% fetal calf serum ("FCS") for 30 min at 37° C. Nonadherent cells were gently washed away [some of these non-adherent cells were also DCs. To collect these DCs, the cells were incubated in RPMI 1640 supplemented with 20% FCS for 30 min to 1 hr. Floating cells were removed. The residual adherent cells were incubated in RPMI 1640 supplemented with 20% FCS for 2–3 days. The loosely adherent cells were DCs. The remaining, adherent cells were incubated with RPMI 1640 supplemented with 10% fetal calf serum overnight. Loosely adherent cells were subsequently collected and cultured in a medium containing GM-CSF (1000 U/ml) and IL-4 (100 U/ml) at a density of $10^6$ cells/ml for 5–6 days. The resultant cells were the DCs used in fusion experiments.

DCs were also obtained from bone marrow stem cell cultures. In brief, stem cells were placed in a flask containing RPMI 1640 supplemented with 10% FCS. After 30 min of incubation at 37° C., nonadherent cells were washed away. Fresh RPMI 1640 supplemented with 10% FCS was added to the remaining, adherent cells. After overnight incubation, loosely adherent cells were collected and incubated in RPMI 1640/10% FCS medium containing GM-CSF (1000 U/ml) and IL-4 (100 U/ml) for 5–6 days; The resultant cells were DCs that were ready for use in fusion.

Cell fusion was carried out between DCs and human myeloma cells MY5 to produce fused cells DC/MY5. After fusion, the cells were placed in HAT selection for 10–14 days. IL-6 was also added to the culture at 20–50 ng/ml to promote survival of DC/MY5 cells. Procedures for fusion were essentially the same as described in Example 1, supra, except that the fused cells were separated from unfused myeloma cells based upon the higher degree of surface adherence exhibited by the fused cells.

Results

As shown in flow cytometry, DC/MY5 cells retained the phenotypic characteristics of their parental cells: DC/MY5 were positively stained by mabs for HLA-DR, CD38 (a myeloma cell-surface marker), DF3 (a tumor cell-surface marker), and CD83 (a DC cell-surface marker), B7-1, and B7-2. MLR assays demonstrated that these fused cells were also potent stimulators of T cells.

EXAMPLE III

Reversal of Tolerance to Human MUC1

Antigen in MUC1 Transgenic Mice Immunized with Fusion Cells

Materials and Methods

MUC1 Transgenic Mice

A C57B1/6 mouse strain transgenic for human MUC1 was established as described by Rowse et al. (Cancer Res. 58:315–321, 1998). 500 ng of tail DNA was amplified by PCR using MUC1 primers corresponding to nucleotides 745 to 765 and nucleotides 1086 to 1065, respectively, to confirm the presence of MUC1 sequences. The PCR product was detected by electrophoresis in a 1% agarose gel (Rowse et al., supra).

Cell Culture and Fusion

Murine (C57B1/6) MC38 and MB49 carcinoma cells were stably transfected with a MUC1 cDNA (Siddiqui et al., Proc. Natl. Acad. Sci. USA 85:2320–2323, 1988; Akagi et al., J. Immunotherapy 20: 38–47, 1997; Chen et al., J. Immunol. 159:351–359, 1997). Cells were maintained in DMEM supplemented with 10% heat-inactivated FCS, 2 mM L-glutamine, 100 U/ml penicillin, and 100 $\mu$g/ml streptomycin. DC were obtained from bone marrow culture and fused to the carcinoma cells as described in Example I, supra.

In vitro T Cell Proliferation

Single cell preparations of spleen and lymph nodes were suspended in RPMI medium supplemented with 10% heat-inactivated FCS, 50 $\mu$M $\beta$-mercaptoethanol, 2 mM L-glutamine, 100 U/ml penicillin, and 100 $\mu$g/ml streptomycin. The cells were stimulated with 5 U/ml purified MUC1 antigen (Sekine et al., J. Immunol. 135:3610–3616, 1985). After 1, 3 and 5 days of culture, the cells were pulsed with 1 $\mu$Ci [$^3$H]thymidine per well for 12 hours and collected on filters with a semi-automatic cell harvester. Radioactivity was quantitated by liquid scintillation.

Generation of $CD8^+$ T Cell Lines

Lymph node cells ("LNC") were suspended in complete RPMI medium containing 5 U/ml MUC1 antigen. Ten U/ml murine IL-2 was added after 5 days of culture. On days 10 and 15, the cells were restimulated with 5 U/ml MUC1 antigen and 1:5 irradiated (30 Gy) syngeneic spleen cells as APCs. T cell cultures were analyzed after removal of dead cells by Ficoll centrifugation and depletion of residual APCs by passage through nylon wool. The T cells were stained with FITC-conjugated antibodies against CD3e (145-2C11), CD4 (H129,19), CD8 (53-6.7), αβTcR (H57-597) and γδTcR (UC7-13D5) (PharMingen). After incubation on ice for 1 hour, the cells were washed, fixed and analyzed by FACSCAN (Becton-Dickinson).

Cytotoxicity Assays

In vitro cytotoxicity was measured in a standard $^{51}$Cr-release assay. Briefly, cells were labeled with $^{51}$Cr for 60 minutes at 37° C. and then washed to remove unincorporated isotope. The target cells ($1\times10^4$) were added to wells of 96-well v-bottom plates and incubated with effector cells for 5 hours at 37° C. The supernatants were assayed for $^{51}$Cr in a gamma counter. Spontaneous release of $^{51}$Cr was assessed by incubation of target cells in the absence of effectors, while maximum or total release of $^{51}$Cr was determined by incubation of targets in 0.1% Triton-X-100. Percentage of specific $^{51}$Cr release was determined by the following equation:

$$\text{percent specific release} = [(\text{experimental} - \text{spontaneous})/(\text{maximum} - \text{spontaneous})] \times 100.$$

Humoral Immune Responses

Microtiter plates were coated overnight at 4° C. with 5 U/well purified MUC1 antigen. The wells were washed with PBS containing 5% horse serum albumin and then incubated for 1 hour with four-fold dilutions of mouse sera. After washing and incubation with goat anti-mouse IgG conjugated to horseradish peroxidase (Amersham Life Sciences), antibody complexes were detected by development with o-phenylenediamine (Sigma) and measurement in an ELISA microplate autoreader EL310 at an OD of 490 nm.

Immunohistology

Freshly removed tissues were frozen in liquid nitrogen. Tissue sections of 5 μm in width were prepared in a cryostat and fixed in acetone for 10 minutes. The sections were then incubated with monoclonal antibody DF3 (anti MUC1), anti-CD4 (H129,19) or anti-CD8 (53-6.7) for 30 minutes at room temperature and then subjected to indirect immunoperoxidase staining using the VECTASTAIN ABC kit (Vector Laboratories).

Results

As shown in Example 1, vaccines derived from fusions of DC and MC38/MUC1 carcinoma cells (FC/MCU1) induce potent anti-tumor immunity. To assess the effects of vaccinating MUC1 transgenic mice with FC/MUC1, the mice were immunized twice with $5\times10^5$ FC/MUC1 and, as controls, with $10^6$ irradiated MC38/MUC1 cells or PBS. After challenge with $10^6$ MC38 or MC38/MUC1 cells, all mice immunized with irradiated MC38/MUC1 cells or PBS developed tumors. By contrast, no tumor growth was observed in mice immunized with FC/MUC1. Immunization of the MUC1 transgenic mice with FC/MUC1 had no effect on growth of the unrelated MB49 bladder carcinoma (Chen et al., J. Immunol. 159:351–359, 1997). However, MB49 cells that express MUC1 (MB49/MCU1) failed to grow in the FC/MCU1-immunized mice.

To extend these results, CTLs from the FC/MUC1-immunized mice were assayed for lysis of target cells. CTLs from MUC1 transgenic mice immunized with irradiated MC38/MUC1 cells or PBS exhibited little if any reactivity against MC38/MUC1 cells. By contrast, CTLs from the mice immunized with FC/MUC1 induced lysis of MC38, MC38/MUC1 and MB49/MUC1, but not MB49, cells. As shown in wild-type mice (Example I, supra), immunization with FC/MUC1 induces immunity against MUC1 and other unknown antigens on MC38 cells. Thus, the demonstration that MB49/MUC1, and not MB49, cells are lysed by CTLs confirms that FC/MUC1 induces a MCU1-specific response. Further, immunization of the MUC1 transgenic mice with FC/MUC1, but not irradiated MC38/MUC1 or PBS, induced a specific antibody response against MUC1.

To determine whether T cells from the MUC1 transgenic mice can be primed to induce an anti-MUC1 response, draining LNC were isolated from mice immunized with irradiated MC38/MUC1 cells or FC/MUC1. The LNC were stimulated with MUC1 antigen in vitro. The results demonstrate that LNC from mice immunized with PBS or irradiated MC38/MUC1 cells fail to proliferate in the presence of MUC1 antigen. In contrast, LNC from mice immunized with FC/MUC1 responded to MUC1 with proliferation. To confirm the induction of CTLs against MUC1, draining LNC were isolated from MUC1 transgenic mice immunized with FC/MUC1 and cultured in the presence of MUC1 antigen and irradiated splenocytes. Cells were analyzed by FACSCAN at the beginning and at 10 to 15 days of culture. The results demonstrate the selection of a predominantly CD8$^+$ T cell population after incubation with MUC1 antigen. Unlike naive T cells from unimmunized MUC1 transgenic mice, these CD8$^+$ T cells exhibited specific CTL activity against MC38/MUC1 and MB49/MUC1 targets. Collectively, the results suggest that immunization with FC/MUC1 reverses unresponsiveness to MUC1 in the MUC1 transgenic mice.

The finding that unresponsiveness to MUC1 can be reversed by immunization with FC/MUC1 suggested that this vaccine could be used to treat disseminated disease in a background of MUC1 expression by normal epithelia. In a treatment model, MC38/MUC1 pulmonary metastases were established by tail vein injection of MC38/MUC1 cells into the MUC1 transgenic mice. Whereas control mice treated with vehicle developed pulmonary metastases, mice immunized with FC/MUC1 on day 2 or 4 had no detectable metastases. These findings indicates that FC/MUC1 immunizations can be used to treat metastatic disease in the MUC1 transgenic mice. Importantly, mice protected against MC38/MUC1 tumor exhibited persistent expression of MUC1 antigen in normal bronchial epithelium and other tissues that express the transgene (Rowse et al., Cancer Res. 58:315–321, 1998). Also, staining of MUC1-positive tissues with anti-CD4 and anti-CD8 antibodies did not show any T cell infiltration.

Reversal of unresponsiveness against a self-antigen in adult mice has potential importance in the field of antitumor immunotherapy. The present example demonstrates that immunization with the DC-tumor fusion cells induces an immune response that is sufficient to achieve rejection of established metastases. Notably, induction of an anti-MUC1 response which confers anti-tumor immunity has little, if any, effect on normal secretory epithelia that express MUC1 at apical borders along ducts. These findings demonstrate that the induction of anti-MUC1 immunity represents an effective strategy for the treatment of MCU1-positive human tumors.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for stimulating an immune system, said composition comprising a plurality of cells at least half of which are fused cells, each of which fused cells is generated by fusion between at least one mammalian dendritic cell and at least one mammalian tumor or cancer cell that expresses a cell-surface antigen, wherein the dendritic cell and the cancer or tumor cell are from the same mammalian species, wherein the dendritic cell can process and present antigens, and wherein at least half of the fused cells express, in an amount effective to stimulate an immune system, (a) a MHC class II molecule, (b) B7, and (c) the cell-surface antigen.

2. The composition of claim 1, wherein the mammalian dendritic cell and the mammalian tumor or cancer cell are obtained from the same individual.

3. The composition of claim 2, wherein the mammalian species is a human.

4. The composition of claim 1, wherein the mammalian dendritic cell and the mammalian tumor or cancer cell are obtained from different individuals of the same species.

5. The composition of claim 4, wherein the species is *Homo sapiens*.

6. A method of stimulating the immune response in an individual, wherein the individual has a condition selected from the group consisting of cancer, and predisposition to develop cancer, said method comprising administering the composition of claim 1 to the individual, wherein an immune response is induced.

7. A method of stimulating the immune response in a human, wherein the human has a condition selected from the group consisting of cancer, and predisposition to develop cancer, said method comprising administering the composition of claim 3 to the human, wherein an immune response is induced.

8. The method of claim 7, wherein the mammalian dendritic cells are obtained from the human or an identical twin of the human.

9. The method of claim 8, wherein the tumor or cancer cells are obtained from the human.

10. The method of claim 8, wherein the cancer antigen is MUC1.

11. The method of claim 10, wherein the human has one of the following conditions or predisposition to develop one of the following conditions: breast cancer, ovarian cancer, pancreatic cancer, prostate gland cancer, lung cancer, and myeloma.

12. A composition for stimulating an immune system, said composition comprising a plurality of fused cells, each of which fused cells is generated by fusion between at least one mammalian dendritic cell and at least one mammalian tumor or cancer cell that expresses a cell-surface antigen, wherein the dendritic cell and the tumor or cancer cell are from the same mammalian species, wherein the dendritic cell can process and present antigens, and wherein a plurality of the fused cells express, in an amount effective to stimulate an immune system, (a) a MHC class II molecule, (b) B7, and (c) the cell-surface antigen.

13. The composition of claim 12, wherein the mammalian dendritic cell and the mammalian tumor or cancer cell are obtained from the same individual.

14. The composition of claim 13, wherein the individual is a human.

15. The composition of claim 12, wherein the mammalian dendritic cell and the mammalian tumor or cancer cell are obtained from different individuals of the same species.

16. The composition of claim 15, wherein the species is *Homo sapiens*.

17. The method of claim 7 wherein the human has at least one antigen in common with the cell-surface antigen expressed by the tumor or cancer cell.

18. A hybrid comprising a human dendritic cell derived from a dendritic cell progenitor and human tumor or cancer cell, wherein said hybrid expresses at least one cell-surface antigen from said tumor or cancer cell, at least one MUC class II molecule, and B7.

* * * * *

UNITED STATES PATENT AND TRADEMARK OFFICE
CERTIFICATE OF CORRECTION

PATENT NO. : 6,652,848 B1
DATED : November 25, 2003
INVENTOR(S) : Gong et al.

It is certified that error appears in the above-identified patent and that said Letters Patent is hereby corrected as shown below:

Column 3,
Line 10, after "cells", delete "(MC38/MCU1)", and insert -- (MC38/MUC1) --.
Line 12, delete "MCU1)", and insert -- MUC1) --.

Column 7,
Line 38, after "DF3", delete "(anti-MCU1)", and insert -- (anti-MUC1) --.
Line 51, after "DCs", delete "MC38/MCU1", and insert -- MC38/MUC1 --.

Column 9,
Line 50, "DCs." should read -- DCs]. --.

Column 11,
Line 45, after "cells", delete "(FC/MCU1)", and insert -- (FC/MUC1) --.
Line 57, after "MUC1", delete "(MB49/MCU1)", and insert -- (MB49/MUC1) --.
Line 58, after "the", delete "FC/MCU1", and insert -- FC/MUC1 --.

Column 12,
Line 3, after "induces a", delete "MCU1", and insert -- MUC1 --.
Line 57, after "treatment of", delete "MCU1", and insert -- MUC1 --.

Column 14,
Line 35, after "at least one", delete "MUC", and insert -- MHC --.

Signed and Sealed this

Twelfth Day of October, 2004

JON W. DUDAS
*Director of the United States Patent and Trademark Office*